(12) United States Patent
Hausmann et al.

(10) Patent No.: US 7,405,328 B2
(45) Date of Patent: Jul. 29, 2008

(54) METHOD FOR PRODUCING ALKENONE ETHERS

(75) Inventors: Eckhard Hausmann, Hannover (DE); Oalf Boese, Hannover (DE); Johannes Eicher, Sehnde-Ilten (DE)

(73) Assignee: Solvay Fluor GmbH, Hannover (DE)

( * ) Notice: Subject to any disclaimer, the term of this patent is extended or adjusted under 35 U.S.C. 154(b) by 45 days.

(21) Appl. No.: 11/294,371

(22) Filed: Dec. 6, 2005

(65) Prior Publication Data

US 2006/0084813 A1    Apr. 20, 2006

Related U.S. Application Data

(63) Continuation of application No. PCT/EP2004/005466, filed on May 21, 2004.

(30) Foreign Application Priority Data

Jun. 6, 2003   (DE) ................ 103 25 715

(51) Int. Cl.
    *C07C 45/46*   (2006.01)
(52) U.S. Cl. ................. 568/319; 568/407; 568/408
(58) Field of Classification Search ............... None
    See application file for complete search history.

(56) References Cited

U.S. PATENT DOCUMENTS 5,708,175 A    1/1998   Koyanagi et al.

OTHER PUBLICATIONS

F. Effenberger et al. "Die Acylierung von Enolethem mit reaktiven Carbonsäurechloriden", Chemische Berichte., vol. 115, 1982, pp. 2766-2782, XP002295515, Verlag Chemie GmbH Weinheim., DE p. 2770—p. 2271—p. 2275.

L, F. Tietze et al., "Synthesis of Alkyl Propanoates by Haloform Reaction of a Trichloro Ketone", Organic Synthesis., vol. 69, 1990, pp. 238-244, XP008037891, USWiley and Sons, New York, NY pp. 238-240.

A. Colla et al., "Trihaloacetylated Enol Ethers—General Synthetic Procedure and Heterocyclic Ring Closure Reactions with Hydroxylamine", Synthesis, Georg Thieme Verlag. Stuttgart, DE Jun. 1, 1991 pp. 483-486, XP000196317, ISSN: 0039-7881 the whole document.

I. I. Gerus et al., "Synthesis and Properties of beta-Ethoxyvinyl Polyfluoroalkyl Ketones", Synthesis., No. 5, 2000, pp. 738-742, XP002295516, Georg Thieme Verlat. Stuttgart., DE the whole document.

P. P. Klemchuk, "Antioxidants: 4. Antioxidant Classes" Online!, Jun. 15, 2000, Wiley-VCH Verlag, XP 002303289, Retrieved from the Internet: URL:http://ww.mrw.interscience.Wiley.com/ueic/articles/a03_091/sect4-fs.html DOI: 10.1002/14356007.a03_091, the whole document.

International Search Report dated Nov. 12, 2004 based on International Application No. PCT/EP2004/005466.

*Primary Examiner*—Sikarl A Witherspoon
(74) *Attorney, Agent, or Firm*—Crowell & Moring LLP

(57) ABSTRACT

In a method or producing haloalkenone ethers by addition of a carboxylic acid halide to a vinyl ether and subsequent elimination of hydrogen halide, the improvement comprising carrying out the reaction in the absence of a base and/or in the presence of a stabilizer for the resulting alkenone, whereby higher yields of the desired alkenone product can be obtained.

10 Claims, No Drawings

METHOD FOR PRODUCING ALKENONE ETHERS

CROSS REFERENCE TO RELATED APPLICATIONS

This application is a continuation of international patent application no. PCT/EP2004/005466, filed May 21, 2004, designating the United States of America and published in German as WO 2004/108647 on Dec. 16, 2004, the entire disclosure of which is incorporated herein by reference. Priority is claimed based on Federal Republic of Germany patent application no. DE 103 25 715.2, filed Jun. 6, 2003.

BACKGROUND OF THE INVENTION

The present invention relates to a simplified method for preparing halogenated alkenone ethers.

Halogenated alkenone ethers, such as 4-ethoxy-1,1,1-trifluoro-3-butenone, are building blocks in chemical synthesis, as disclosed, for example, in U.S. Pat. No. 5,708,174 (=EP 744,400). They may be prepared by reacting an acid chloride with a vinyl ether in the presence of a base, as described in the aforementioned U.S. patent. For this reaction, the base may also be used in excess as a solvent. It is known, for example, from N. D. Field and D. H. Lorenz, High Polymer, 1970, page 394 that the reaction of phosgene with vinyl ethers in the absence of a base leads to polymerization.

SUMMARY OF THE INVENTION

It is an object of the present invention to provide a simplified method for the preparation of alkenones.

This and other objects are achieved by providing a method for preparing an alkenone, said method comprising reacting a carboxylic acid halide with a vinyl ether in an addition reaction, and subsequently eliminating hydrogen halide to form the alkenone, wherein the reaction is carried out in the absence of an acid-capturing agent for the resulting hydrogen halide, or in the presence of a stabilizer for the resulting alkenone.

To carry out the method of the invention for the preparation of alkenones, vinyl ether and carboxylic acid halide, preferably carboxylic acid chloride, are reacted with one another in the absence of an acid-capturing agent and/or in the presence of a stabilizer for the alkenone. The term "acid-capturing agent" comprises, in particular, bases, especially nitrogen bases such as pyridine or secondary and tertiary amines, as well as onium salts, which are described in the international patent application, which has not been pre-published and carries the application number PCT/EP 03/00913. However, the use of this term should not be interpreted as an attempt to explain the invention.

A preferred embodiment of the invention is the preparation of alkenones which are substituted at the carboxylic acid group with halogen, especially with fluorine and/or chlorine. The preparation of alkenones corresponding to Formula (I):

$$R^1-C(O)-C(H)=C(H)-OR^5 \qquad (I)$$

is particularly preferred. In the above Formula (I), $R^1$ represents a C1-C4 alkyl group or a C1-C4 alkyl group which is substituted by at least one halogen atom or $R^1$ represents $CF_3C(O)CH_2$ and $R^2$ represents aryl, substituted aryl, a C1-C4 alkyl group or a C1-C4 aryl group, which is substituted by at least one halogen atom.

For the method of the invention, an acid halide corresponding to Formula (II):

$$R^1-C(O)X \qquad (II)$$

in which X represents fluorine, chlorine or bromine and $R^1$ has the meaning given above, is reacted with a vinyl ether corresponding to Formula (III):

$$CH_2=C(H)-OR^2 \qquad (III)$$

in which $R^2$ has the meaning given above, in the absence of an acid-capturing agent and/or in the presence of a stabilizer for the alkenone.

$R^1$ preferably represents methyl, ethyl, n-propyl, isopropyl or methyl, ethyl, n-propyl or isopropyl substituted by at least one fluorine atom. It is especially preferred if $R^1$ represents methyl, ethyl or methyl or ethyl substituted by at least one fluorine atom. $CF_3$, $CF_2H$, $CF_2Cl$, $C_2F_5$, $C_3F_7$ or $CF_3C(O)CH_2$ are particularly preferred as $R^1$.

$R^2$ may represent aryl, for example, phenyl or C1-C4 alkyl groups and/or phenyl substituted by halogen atoms. Preferably, $R^2$ represents a linear or branched C1-C4 alkyl group, and particularly preferably $R^2$ represents methyl, ethyl, n-propyl or isopropyl.

An acid chloride is preferred as the acid halide. The invention will be explained in further detail hereinafter with reference to this preferred embodiment.

The molar ratio of acid chloride to vinyl ether preferably is between 0.8:1 and 1:0.8, and particularly preferably between 0.8:1 and 1:1.

The method of the invention may advantageously be carried out in two steps. In the first step, the acid halide is added to the vinyl ether. The reaction may be exothermic, so that it may be necessary to cool the reaction mixture or to carry out the reaction very slowly. If a low boiling acid halide is used, it is advantageous to use a condenser, which condenses the acid halide, making a return of the acid halide to the reaction mixture possible. This step is preferably carried out at −15° C. to +50° C., and particularly preferably at −15° C. to +30° C.

Step 2 comprises the elimination of hydrogen halide. It is advisably carried out at the temperature necessary for the elimination, which can easily be ascertained by observing the splitting off of the hydrogen halide. In the reaction of trifluoroacetyl chloride with ethyl vinyl ether, the temperature lies in the range of up to 150° C., and preferably in the range from 30° C. to 90° C.

Preferably, a solvent is not used for the reaction between the acid halide and the vinyl ether in accordance with the invention. This has the advantage that a solvent does not have to be removed, so that the expense of recovering the desired product is reduced and less energy is required to carry out the method.

The method according to the invention for preparing alkenones of Formula (I) can be carried out at an elevated pressure. Atmospheric pressure or a slight vacuum (down to 0.5 bar) is of advantage, because the hydrogen halide formed can be removed better from the reaction mixture. The method also can be carried out batchwise or partly continuously. The hydrogen halide which forms can be removed from the reaction mixture during or after the reaction, for example, by heating or applying a vacuum, or both.

The method according to the invention comprises three variations, namely the reaction in the absence of an acid-capturing agent (this concept also includes an onium salt), the reaction in the presence of a stabilizer for the desired product (the alkenone), and finally the reaction with both features, namely the absence of the acid-capturing agent and the presence of the stabilizer. For example, phenols, substituted with a plurality of alkyl groups, such as two t-butyl groups and one phenol-substitued alkyl group with 1 to 3 carbon atoms, especially 2,6-di-t-butyl-4-methylphenol, are suitable as stabilizers.

The reaction, carried out in the presence of a stabilizer for the alkenone that is to be produced, can also be carried out in the presence of conventional acid-capturing agents such as amines, onium salts or appropriate solvents, such as nitrites, sulfoxides or lactams. This variation represents an improvement of the known method which is subject to the disadvantages of the occurrence of salts and the need to remove a solvent.

The two other variations, reacting in the absence of an acid-capturing agent or the reaction in the absence of an acid-capturing agent and in the presence of a stabilizer for the alkenone which is to be produced, are far more advantageous than the method of the state of the art, because the acid-capturing agent does not have to be removed. These two variations are preferred and are explained further.

According to the one preferred variation, the starting compounds are reacted generally in the absence of an acid-capturing agent for the alkenone. The concept of "acid-capturing agent" is defined further above.

According to the other of the two preferred variations, the starting compounds are reacted in the absence of an acid-capturing agent, but in the presence of a stabilizer for the alkenone which is to be produced. For example, phenols, substituted with a plurality of alkyl groups, such as two t-butyl groups and one phenol-substituted alkyl group with 1 to 3 carbon atoms, especially 2,6-di-t-butyl-4-methylphenol, are suitable as stabilizers.

The two last-mentioned variations, the characteristic feature of which is the absence of an acid-capturing agent, are preferred, as stated above.

The reaction mixture can be worked up by conventional methods. For example, the desired alkenone of Formula (I) can be distilled from the mixture.

An advantage of the method according to the invention is that the working up is facilitated in the absence of an acid-capturing agent. The presence of a stabilizer for the alkenone already in the reaction mixture helps to increase the yield. The absence of an acid-capturing agent and the simultaneous presence of a stabilizer for the alkenone in the reaction mixture may be very advantageous for the yield.

EXAMPLES

The following examples are intended to illustrate the invention in further detail without limiting its scope.

Example 1

Reaction between ethyl vinyl ether and trifluoroacetyl chloride to form 4-ethoxy-1,1,1-trifluoro-3-buten-2-one ("ETFBO") in the absence of an acid-capturing agent and in the presence of a stabilizer for the alkenone that is to be prepared.

Formulation:
0.25 g (1.13 mmoles) of 2,6-di-t-butyl-4-methylphenol ("BHT")
12.9 g (99%, 0.18 moles) of ethyl vinyl ether ("EVE")
21.0 g (0.16 moles) of trifluoroacetyl chloride ("TFAC")

Procedure:
BHT and EVE were mixed together. Then TFAC was introduced into the mixture in an ice bath under a reflux condenser cooled with dry ice. The temperature of the reaction mixture was kept below 26° C. Subsequently, the reaction mixture was thermolyzed at 80° C. After the thermolysis, the reaction mixture still weighed 28.5 g and was then distilled at 9 mbar. The yield was 24.1 g, which corresponded to 83.0% of the theoretical yield.

Upon repetition of the procedure 0.25 g of BHT, 13.8 g of EVE and 19.7 g of TFAC, a yield of 87.6% of the theoretical was obtained.

Example 2

Preparation of ETFBO Without a Stabilizer

Formulation:
13.0 g (99%, 0.19 moles) of EVE
19.1 g (0.14 moles) of TFAC

Procedure:
The EVE was added to the reaction flask and, under cooling with dry ice, TFAC was added at room temperature. Subsequently, the product was thermolyzed at 80° C. and the thermolyzed mixture was then distilled at 7 mbar. The yield was 22.8 g, which corresponded to 90.4% of the theoretical yield.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method for preparing an alkenone, corresponding to Formula (I):

$$R^1-C(O)-C(H)=C(H)-OR^2 \qquad (I)$$

in which
$R^1$ represents $CF_3$, and
$R^2$ represents aryl, substituted aryl, a C1-C4 alkyl group or a C1-C4 alkyl group, which is substituted by at least one halogen atom;
said method comprising reacting a carboxylic acid halide with a vinyl ether in an addition reaction in a first step, and subsequently eliminating hydrogen halide in a second step to form the alkenone, wherein the reaction is carried out in the absence of an acid-capturing agent for the resulting hydrogen halide, and the second step is carried out at a temperature in the range from 30° C. to 90° C.
wherein the acid halide corresponds to Formula (II):

$$R^1-C(O)X \qquad (II)$$

in which
X represents fluorine, chlorine or bromine, and
$R^1$ has the meaning given above,
and the vinyl ether corresponds to Formula (III):

$$CH_2=C(H)-OR^2 \qquad (III)$$

in which $R^2$ has the meaning given above.

2. A method according to claim 1, wherein $R^2$ represents methyl, ethyl, n-propyl or isopropyl.

3. A method according to claim 1, wherein the reaction is carried out in two steps, the first step comprising reacting the acid halide with the vinyl ether in an addition reaction, and the second step comprising eliminating hydrogen halide to form the alkenone.

4. A method according to claim 3, wherein the first step is carried out at a temperature in the range from −15° C. to +50° C., and the second step is carried out at a temperature ranging up to 150° C.

5. A method according to claim 4, wherein the first step is carried out at a temperature in the range from −15° C. to +30° C.

6. A method according to claim 1, wherein the molar ratio of vinyl ether to carboxylic acid chloride ranges from 0.8:1 to 1:0.8.

7. A method according to claim 6, wherein the carboxylic acid chloride is used in a less than stoichiometric amount.

8. A method according to claim 1, wherein the reaction is carried out in the presence of a stabilizer for the resulting alkenone.

9. A method according to claim 8, wherein said stabilizer comprises a phenol substituted by at least one C1--C5 alkyl group.

10. A method according to claim 9, wherein said stabilizer comprises 2,6-di-t-butyl-4-methylphenol.

* * * * *